United States Patent [19]

Elmerick et al.

[11] Patent Number: 5,300,752
[45] Date of Patent: Apr. 5, 1994

[54] NEEDLE DISINTEGRATION DEVICE METHOD AND APPARATUS

[76] Inventors: Donald Elmerick, 466 Spring Grove Dr.; Richard Peters, 814 Pennwood Dr., both of Tallmadge, Ohio 44278

[21] Appl. No.: 57,818
[22] Filed: May 7, 1993
[51] Int. Cl.$^5$ .............................................. B23K 11/22
[52] U.S. Cl. .................................................... 219/68
[58] Field of Search .......................................... 219/68

[56] References Cited

U.S. PATENT DOCUMENTS

| | | |
|---|---|---|
| 4,628,169 | 12/1986 | Ch'ing-Lung ............... 219/68 |
| 4,877,934 | 10/1989 | Spinello ....................... 219/68 |
| 4,961,541 | 10/1990 | Hashimoto ................... 219/68 |
| 4,965,426 | 10/1990 | Colombo ..................... 219/68 |
| 5,076,178 | 12/1991 | Kohl et al. ................... 219/68 |
| 5,091,621 | 2/1992 | Butler ........................... 219/68 |
| 5,138,124 | 8/1992 | Kirk et al. .................... 219/68 |
| 5,138,125 | 8/1992 | Salesses ........................ 219/68 |
| 5,212,362 | 5/1993 | Burden et al. ................ 219/68 |

*Primary Examiner*—Geoffrey S. Evans

[57] ABSTRACT

A method and apparatus for disintegrating and otherwise destroying a syringe needle through total and complete incineration. This apparatus being contained within a housing having an orifice through which a syringe needle is continuously inserted, engaging a first conductive plate shaped and positioned so as to accept a vast majority of all commercial needles, then engaging a movable second conductive plate movable within the housing from a first position immediately adjacent to the first conductive plate to a second position commensurate to the length of said needle, actuating a switch which, when closed, permits an electric current to emanate from a suitable power source to pass between a first and second electrical contact disposed upon the first and second conductive plates such that the needle is subjected to electrical current sufficient to immediately disintegrate it along its entire length with a resultant caplike mushroom cover at the distal end of the needle remnant effectively eliminating needle reuse or leakage of mediation or body fluid.

10 Claims, 6 Drawing Sheets

NEEDLE DISINTEGRATION DEVICE METHOD AND APPARATUS

BACKGROUND AND SUMMARY OF THE INVENTION

The instant invention deals and otherwise relates to a needle disintegration device. More importantly, the instant invention involves an apparatus which is important to medical safety in general and resolves several problematic aspects of syringe needle disposal. The vast majority of all syringes used in the medical community are, indeed, disposable in nature. These syringes are utilized to inject medications and draw fluids for miscellaneous testings and other medical procedures. Once utilized, a used syringe should ideally be disposed of in such a manner as to not create the possibility of contamination or injury to a third party. In particular, used syringe needles always pose the possibility of "sticking" an unintended individual. Residual medication and/or body fluids are then capable of being passed into an unintended or unsuspecting individual. It is medically well understood that this potentiality of fluid transmission is incredibly dangerous. Transmission of infectious hepatitis, AIDS (Acquired Immune Deficiency Syndrome), and other catastrophic and dangerous diseases or afflictions are quite capable of being transmitted in this manner.

The instant device accomplishes complete incineration of the needle at temperatures in the neighborhood of 1,000° C. to 2,000° C. It is believed and understood that incineration at such extreme temperatures attenuates or otherwise destroys nearly any pathogen.

Additional societal concerns are also addressed and remedied by the within invention. One of the greatest of these concerns is the possibility of syringes secondarily being used by drug addicts and for other unlawful and unsavory purposes.

An ideal needle destruction means would accomplish resolution of both of the foregoing problem areas and other foreseeable difficulties. Specifically, it would eliminate the hazard posed by the possibility of a needle "stick" and also eliminate any possibility of reuse by addicts and for other unintended purposes.

In the past few years, there have been several advancements in needle disposal techniques. Initially, some of these measures involved the simple shearing of the syringe to separate the needle from the syringe housing. Unfortunately, however, this did not adequately address the issue of the possibility of a needle "stick" to an individual thereby possibly transmitting disease or unwanted medication. Further, these methods often left a needle remnant of sufficient quantity to allow syringe reuse. Additional methods have involved incineration and grinding of syringes to address needle destruction. Unfortunately, however, none of these methods have been sufficient to accomplish all of the aforesaid objects and desires. They result in either leftover needle sheathing, a modicum of an opening through which medicines and/or fluids continue to pass, or disposal of a syringe needle wherein residual bacteria or other pathogens continue to exit in the needle remnants.

It is, therefore, a principal object of the within invention to accomplish all of the foregoing objects and desires through the utilization of a needle disintegrating device which totally and completely destroys the entire length of a syringe needle and, due to the nature of disintegration, provides a caplike mushrooming on the needle remnant so as to eliminate the possibility of needle "stick" or continued use of the syringe.

It is a further object of the within to provide an apparatus which is safe and economically viable in operation and capable of use on a vast majority, if not all, of the syringe needle lengths, shapes, and diameters in the marketplace.

In the preferred embodiment of the within invention, a syringe disintegration device comprises a generalized housing containing the incineration elements. The housing has an orifice through which nearly any sized syringe needle may be inserted into the interior of the housing. Upon insertion into the housing, the syringe needle first comes in contact with a first conductive plate shaped so as to receive a plurality of syringe needle sizes and diameters. As one pushes the syringe into the housing orifice the needle tip then engages a second conductive plate which is disposed so as to be axially movable between a first and second position. The distance between the first and second position is of sufficient distance so as to accept all, or a vast majority, of needle lengths in use in the marketplace. The first and second conductive plates are equipped with first and second electrical contacts and are electrically compatible to enable the passage of current as between them. Electrical current is actuated when a needle is completely inserted into the housing orifice and the needle hub comes in contact with the first conductive plate which flexes and pressure actuates a switching mechanism. Thereupon, an electrical current is passed between the first and second conductive plates by means of a power source consisting generally of standard electrical current modified by a transformer to the eight to fifteen volt range. Additionally, movement of the second conductive plate from its first position opens a circuit allowing current flow to a light or sound emitting mechanism intended to indicate operation and a time relay actuated exhaust fan. Remnants of the needle fall into the bottom of the housing and are collected therein for subsequent disposal as harmless trash due to their innocuous and safe character.

A review of the within invention and drawings will indicate there are numerous other applications and or objects to be accomplished, many of which will become obvious and evident upon review of the within specifications, drawings and other data contained and comprising this Application. It will be seen that the apparatus and the methods thereof accomplish needle disintegration in a novel and unique manner differentiating substantially from the prior art and other devices characteristically used for the aforesaid purpose.

DETAILED DESCRIPTION OF THE DRAWINGS

Figure 1:
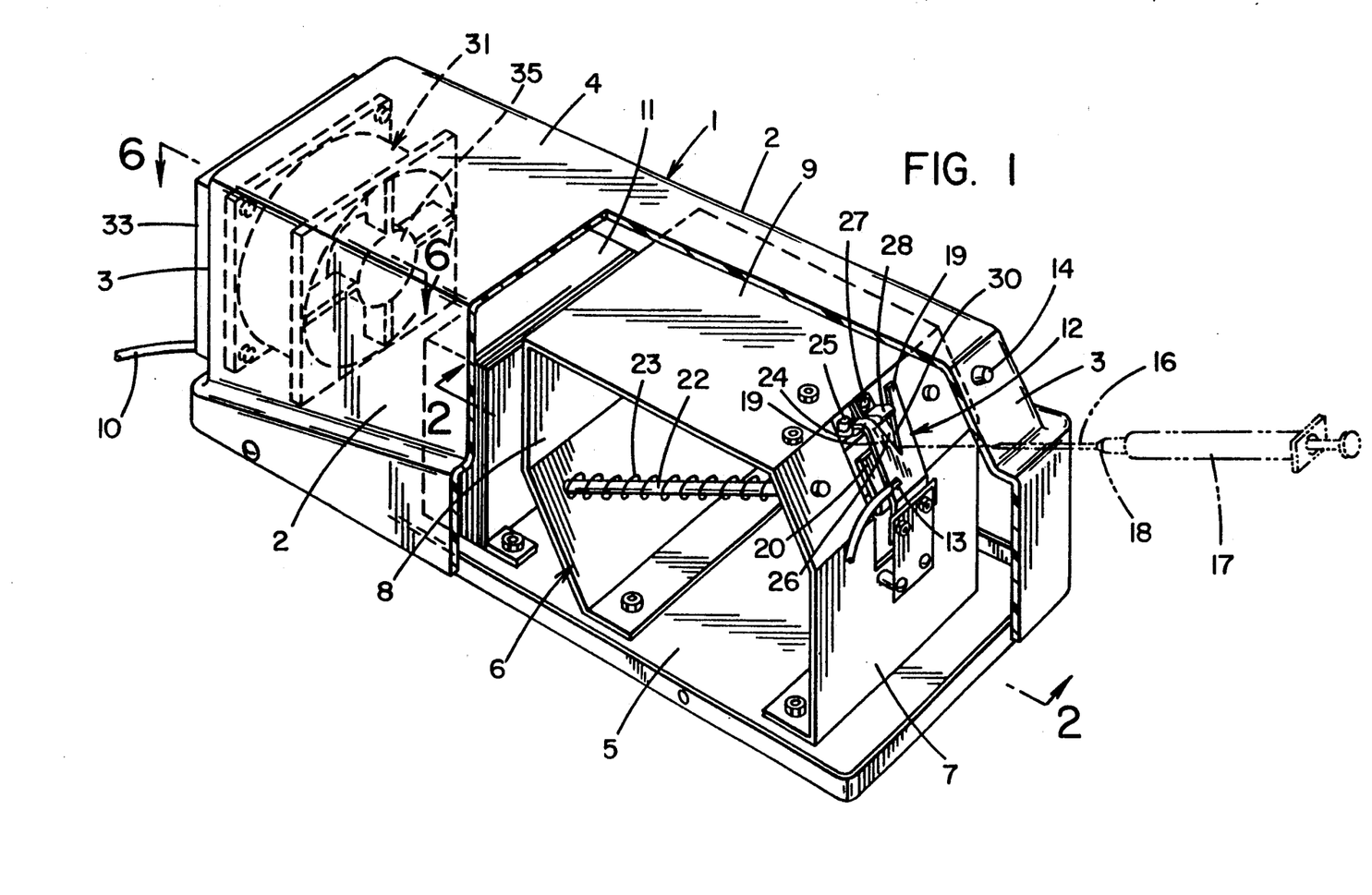
FIG. 1 depicts a view of the claimed apparatus with a cut away section showing several aspects thereof including the incineration mechanism.

FIG. 1 demonstrates a majority of the functional aspects of the claimed apparatus. Collectively, the incineration mechanism is encompassed within a housing 1 constructed of metal, plastic, or other suitable heat resistant material.

The housing 1 is generally rectangular in shape having side walls 2, end walls 3, a top 4, and bottom 5. A housing bracket 6 is securely attached to the bottom 5 of housing 1 and consists generally of a front wall 7, a back wall 8, and a top 9. Said housing bracket 6 preferably made of heavy, nonflexible and nonconductive material as it should be electrically neutral throughout operation. Housing bracket 6 as depicted in FIG. 1 has been constructed of metal and, accordingly, all potential electrical contact points throughout have been shielded by the incorporation of insulating devices as hereinafter seen or recited. Emanating from an end wall 3 of housing 1 is a power cord 10 which may be plugged into any standard receptacle and supplies a transformer 11 for transforming voltage into the eight to twelve volt range. Said transformer 11 being attached to bottom 5 of housing 1. Other ranges of voltage accomplish disintegration, but the aforesaid have been found to be preferred for the within apparatus. Also, other power sources such as batteries of requisite voltage may be used instead of standard electrical power.

A first conductive plate 12 is affixed by screw or other means to front wall 7 of housing bracket 6. The unique "V" shaped configuration of the first conductive plate 12 is readily discernable in FIG. 1. First conductive plate 12 is machined and configured so as to have a pair of leg portions 19 defining a "V" shaped channel 30 into which a needle is inserted and, ultimately, comes to rest. This configuration is crucial in that it enables virtually all sizes of needles to be inserted therein while guaranteeing a particular needle shaft remains in integral contact with first conductive plate 12 thereby allowing current flow into the portion of the needle in harmony with said first conductive plate 12. Finally, the relative location of flash back inhibitor 26 is visible as being affixed to front wall 7 of housing bracket 6 and between first conductive plate 12 and a second conductive plate 20.

A portion of front wall 7 of housing bracket 6 has been eliminated to permit passage through first conductive plate 12 and into the interior of the space generally defined by housing bracket 6. A first electric contact 13 is engaged and positioned upon first conductive plate 12. FIG. 1 also depicts light 14 which is actuated during the incineration process to signal system operation. In the preferred apparatus, a light 14 is utilized, however, any light or sound emitting device may be incorporated into the within apparatus.

Figure 2:
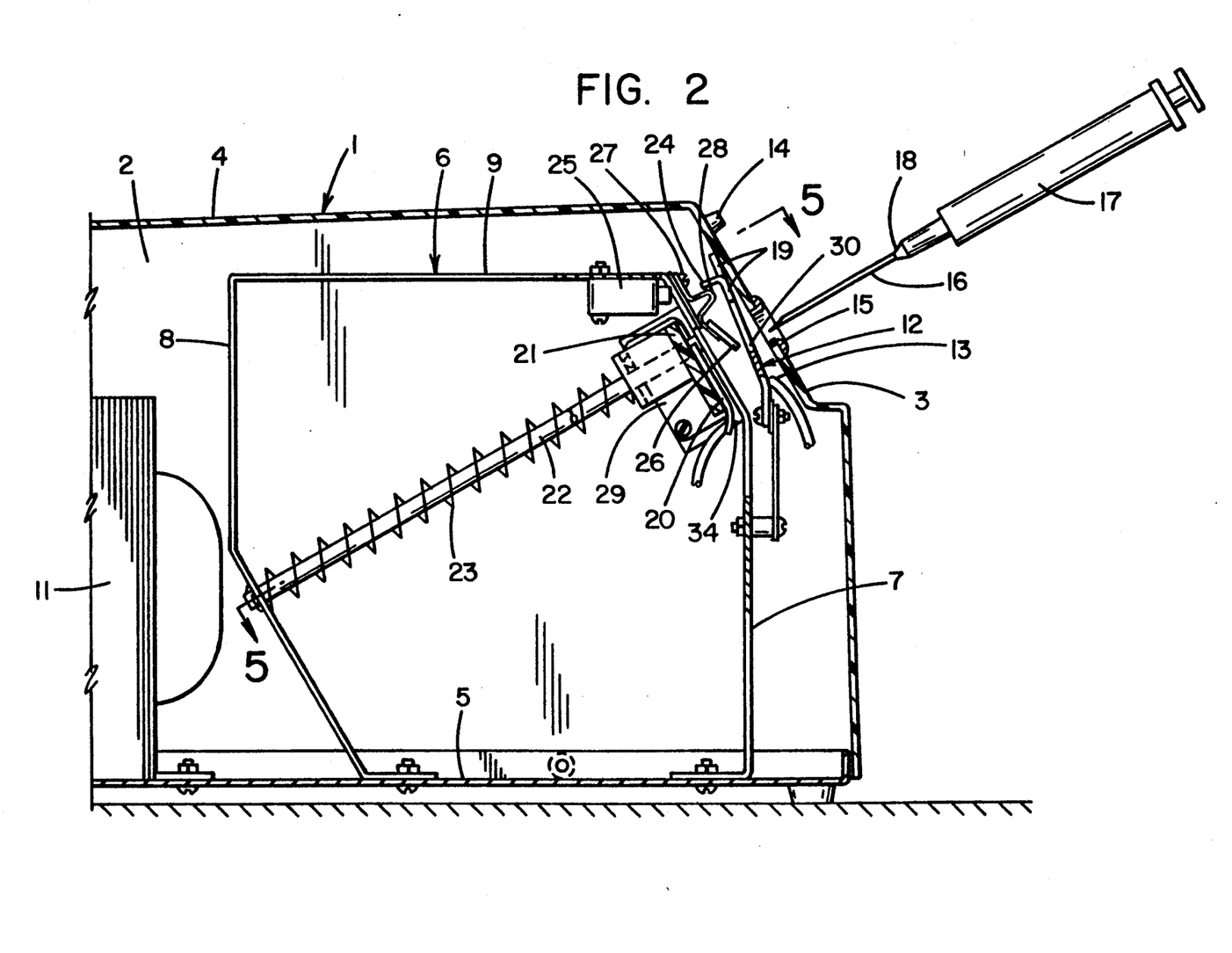
FIG. 2 shows a partial side view of the apparatus and most importantly, the incineration mechanism with a needle poised for insertion.

In preparation for operation, FIG. 2 depicts a needle shaft 16 being inserted into an orifice in housing 1 as defined by grommet 15 which guides the tip of needle shaft 16 into and through the orifice. Immediately thereafter, grommet 15 is spatially arranged so as to direct the needle into contact with first conductive plate 12. A typical syringe needle consists generally of a metallic needle shaft 16, needle body 17, and needle hub 18, normally composed of plastic or other nonconductive material. Due to the configuration of first conductive plate 12, the leg portions 19 thereof engage needle shaft 16 immediately after insertion into grommet 15. Second conductive plate 20 is spatially arranged so as to be immediately adjacent and substantially parallel to first conductive plate 12. Second conductive plate 20 is made from durable conductive metal and secured by screw or adhesive means to escort block 21 constructed of plastic or other non conductive matter. FIG. 2 then clearly depicts the movable mounting aspect of second conductive plate 20 through means of escort rods 22 encased in springs 23 so as to provide second conductive plate 20 biased in close proximity to first conductive plate 12 while in its first position as depicted in FIG. 1. Escort rods 22 are secured by means of attachment to front wall 7 and back wall 8 of housing bracket 6. Escort block 21 is slidably adapted to escort rods 22 to enable complete range of traverse for entire escort rods 22 length. It is imperative to establish escort rods 22 at an angle complementary to the angle of needle insertion so that second conductive plate 20 traverses the length of escort rods 22 in substantially parallel configuration as to first conductive plate 12. In operation, escort rods 22 dictate the length of needle size capable of disintegration. The length of said escort rods 22 are, obviously, a function of the distance between front wall 7 and back wall 8 of housing bracket 6 and, accordingly, the ultimate length and depth of side walls 2, end walls 3, top 4, and bottom 5, of housing 1. Therefore, any needle length could be accommodated but it has been found that escort rods 22 in the length of 5 inches have been adequate to accommodate nearly all needles in current use.

FIG. 2 also teaches the bent or curved nature of the inwardly curving leading edge 24 on one aspect of leg portions 19 and its proximity to actuator switch 25. The first conductive plate 12 is manufactured of conductive metal of a quality and thickness and mounted such that it is capable of bending or flexing inwardly upon pressure and contact from needle hub 18 thereby causing inwardly curving leading edge 24 to engage actuator switch 25. Finally, FIG. 2 shows flash back inhibitor 26 secured to housing bracket 6 by screw and insulator means 27. Its location and configuration allows first conductive plate 12 to compress upon it thereby forcing it inward and into contact with needle shaft 16. Further, curved arm 28 thereof is rigid but still flexible enough to allow compression along its axis upwardly towards screw and insulator means 27 thereby enabling flash back inhibitor 26 to remain in integral contact with larger diameter needles. The physical location in close, if not intimate, contact with needle shaft 16 at the time of incineration reduces or eliminates "flashback" and needle particulates from being propelled back through grommet 15 and onto a user or apparatus surroundings. It further acts to direct needle shaft 16 downward to force and maintain contact with first conductive plate 12 and also direct needle remnants downward onto bottom 5 of housing 1 for ultimate collection.

Figure 3:
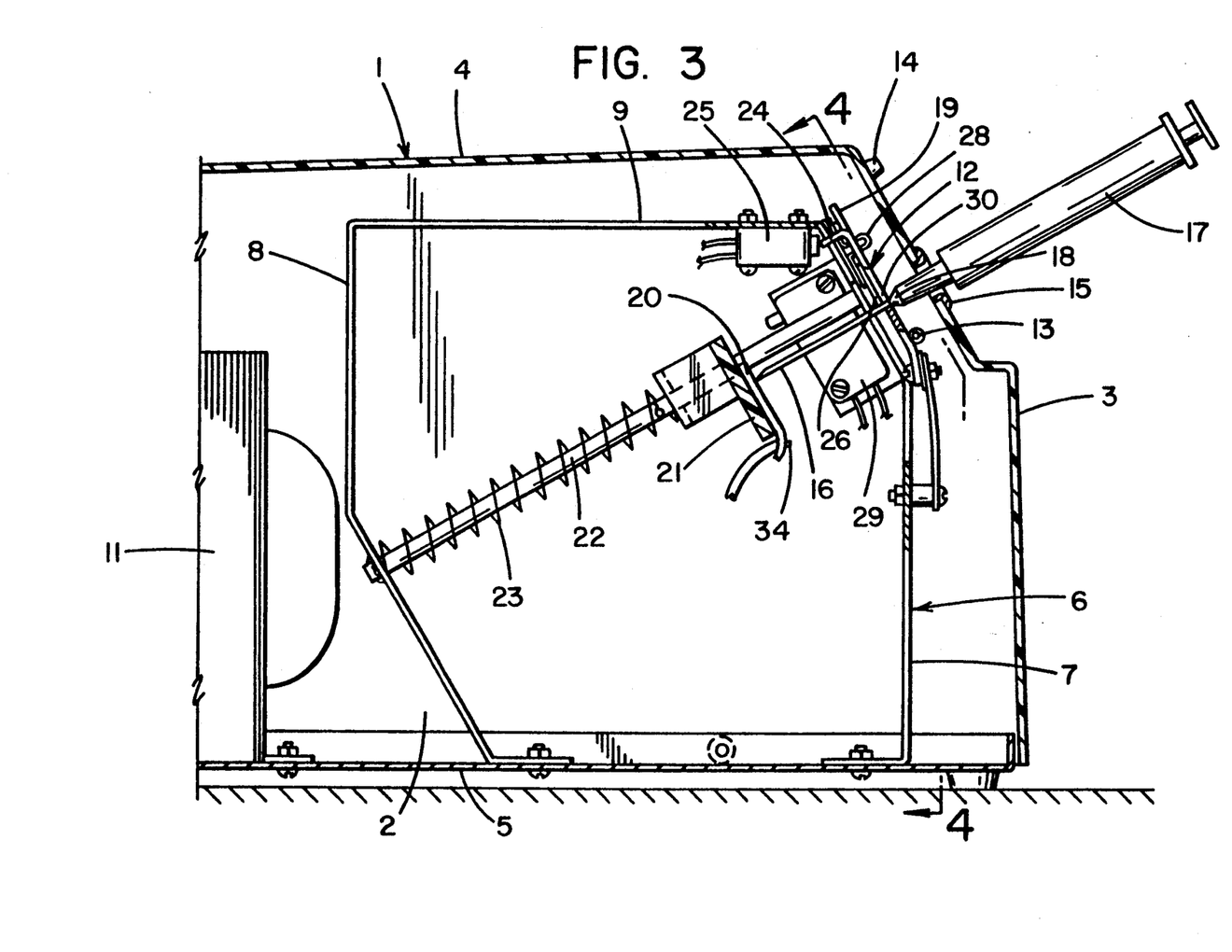
FIG. 3 shows a partial side view of the apparatus with a needle inserted into the incineration mechanism.

FIG. 3 represents the apparatus in operation with needle shaft 16 fully inserted into grommet 15 and first conductive plate 12 flexed inwardly towards front wall 7 of housing bracket 6. As a result of such movement of the first conductive plate 12, the inwardly curving leading edge 24 engages actuator switch 25. Further, flash back inhibitor 26 is compressed by first conductive plate 12 and may be seen impinging upon needle shaft 16. It is important to note that needle hub 18 rests firmly against first conductive plate 12. Needle hub 18 acts as a "stop" to ensure total needle shaft 16 disintegration and the "V" shaped configuration of first conductive plate 12 ensures good, viable and solid surface contact as between needle shaft 16 and the aforesaid first conductive plate 12. Absent the aforesaid configuration, needle hub 18 could pass into the plane of first conductive plate 12 thereby destroying and/or eliminating any possibility of current flow because of the customary non metallic nature of needle hub 18. FIG. 3 also demonstrates the location of second conductive plate 20 with reference to a needle tip and first conductive plate 12. In particular, it can be seen that second conductive plate 20 has now moved away from first conductive plate 12 on escort rods 22 through compression of springs 23. It can also be seen that the location of second conductive plate 20 is now reflective of the absolute length as between a needle tip and the distal end of needle hub 18. Also, second electrical contact 34 may be seen as attached to the second conductive plate 20 as means for passage of electrical flow into second conductive plate 20. Further, FIG. 3 clearly depicts a second actuator switch 29. As second conductive plate 20 withdraws from its first position, second actuator switch 29 is activated thereby enabling current flow to light 14.

Figure 4:
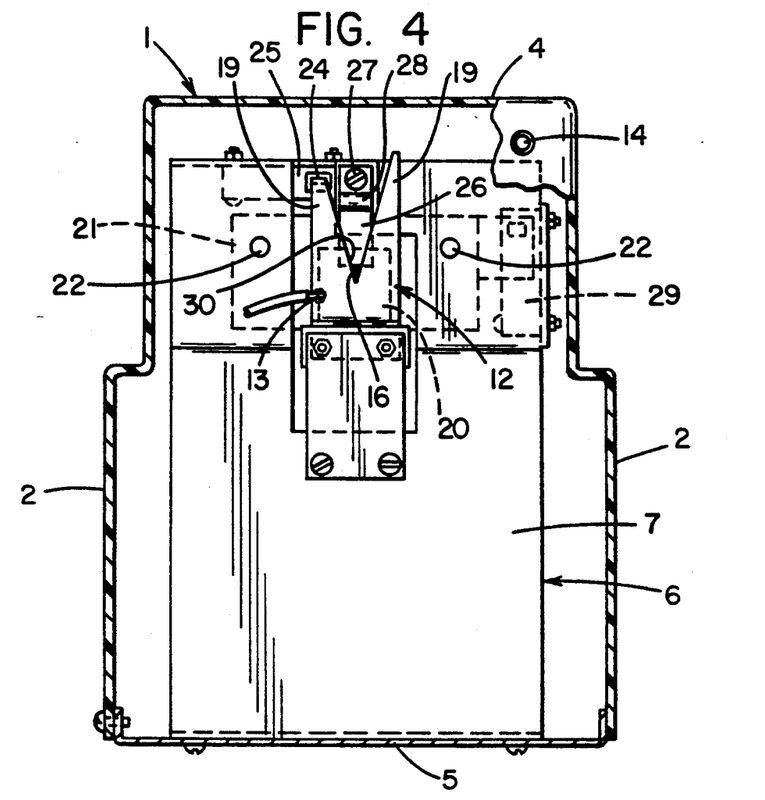
FIG. 4 is a section end view of the apparatus.

FIG. 4 depicts a view of housing 1 from its frontal aspect and portrays the "V" shape configuration of first conductive plate 12 and first electrical contact 13. Additionally, leg portions 19 are readily observable and the shortening of one of the aforesaid leg portions 19 created by the inwardly curving leading edge 24 thereof.

Figure 5:
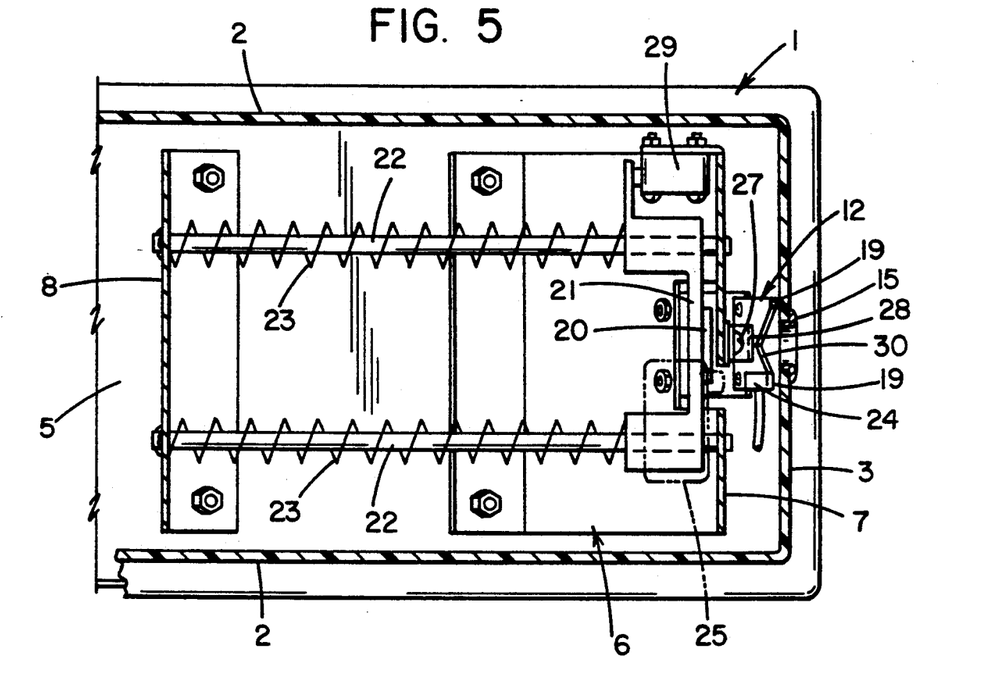
FIG. 5 shows the apparatus in a top view demonstrating the incineration mechanism.

FIG. 5 is a comprehensive view downward upon housing 1 depicting the incineration elements and the spatial arrangement thereof.

Figure 6:
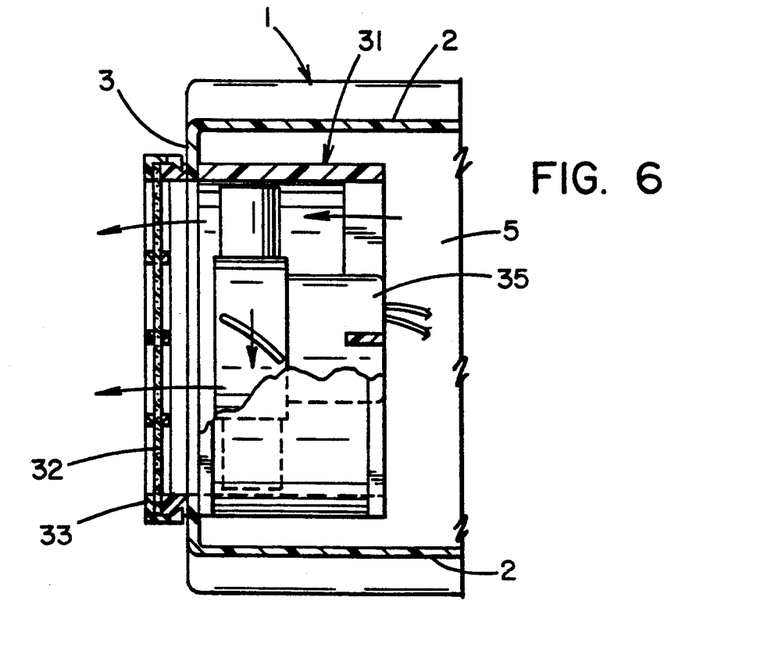
FIG. 6 is a partial side section view through the portion of the apparatus depicting the exhaust fan, filter and exhaust motor.

FIG. 6 is a cross sectional view of the rear of the apparatus and, specifically, end wall 3 of housing 1. Exhaust fan 31 may be observed with exhaust motor 35, and filter 32 encased in filter housing 33 securely affixed onto end wall 3. In the preferred embodiment of the within invention, exhaust fan 31 has a clearance rating of 25 to 35 c.f.m. The aforesaid rating has been found to be preferable, but any rating commensurate therewith is acceptable so that exhaust fan 31 accomplishes its task. Specifically, exhaust fan 31 is intended to remove or alleviate any smoke or other toxins from the interior of the housing 1. It has been found that the aforesaid exhaust fan sizing accomplishes this goal adequately. Further, aforesaid exhaust fan 31 is of sufficient rating to propel air sufficiently through filter 32 to accomplish the foregoing objects and desires. Filter 32 of the within invention is of a certain type as dictated by various governmental or administrative agencies and inclined to alleviate and otherwise trap any airborne pathogens or other resultant unwanted materials which occur from the incineration process. In the preferred embodiment of the within invention, exhaust fan 31 has been found to be most effective when coupled with fan time delay 36. This enables exhaust fan 31 to run for a period of time, preferably ten to twenty seconds, following the termination of electrical current through the electrical circuitry to the aforesaid fan time delay 36. This has the force and effect of continuing to remove fumes and other gases from within housing 1 following termination of the incineration process. Obviously, other time periods for time delay may be utilized but the foregoing seem to accomplish total exhaust capabilities in the stated time frame.

Figure 7:
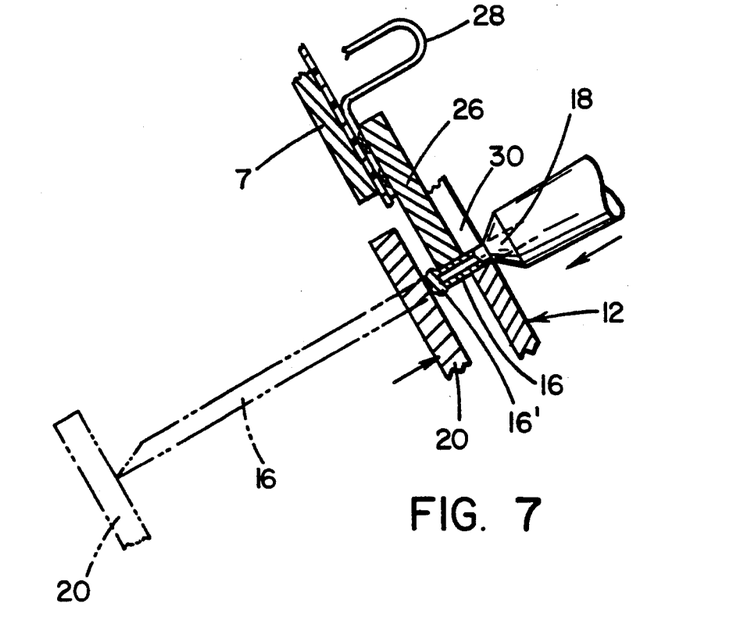
FIG. 7 is an expanded side view demonstrating the remnants of a needle shaft immediately after the incineration process.

FIG. 7 is an expanded view of the configuration of remnants of needle shaft 16 immediately after the incineration process. Specifically, second conductive plate 20 has traversed escort rods 22 on its way back to its first position. Additionally, flashback inhibitor 26 may be seen in its compressed state in contact with first conductive plate 12 and needle hub 18. More importantly, FIG. 7 depicts the caplike mushrooming 16' obtained at the distal most remnant of needle shaft 16' after the incineration process. This caplike mushrooming 16 is very important because it substantially accomplishes two of the desired objects and goals of the within invention. Specifically, it alleviates any possibility of needle reuse and, due to the incineration process and configuration of the aforesaid elements, totally fuses needle shaft 16 to destroy any possibility of fluid or liquid flow out of needle body 17.

Figure 8A:
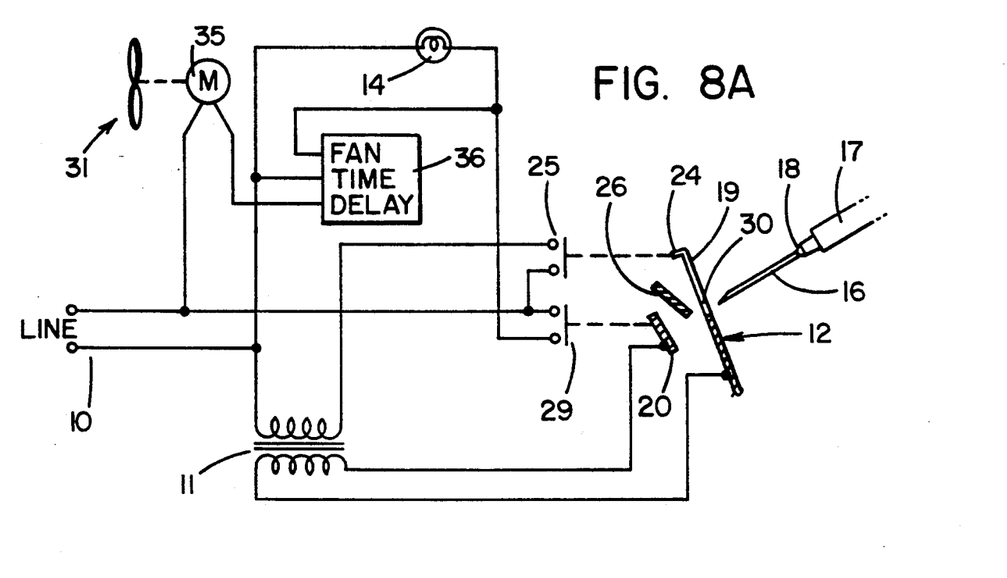
FIGS. 8A and 8B depict the electrical circuitry scheme of the within apparatus.
Figure 8B:
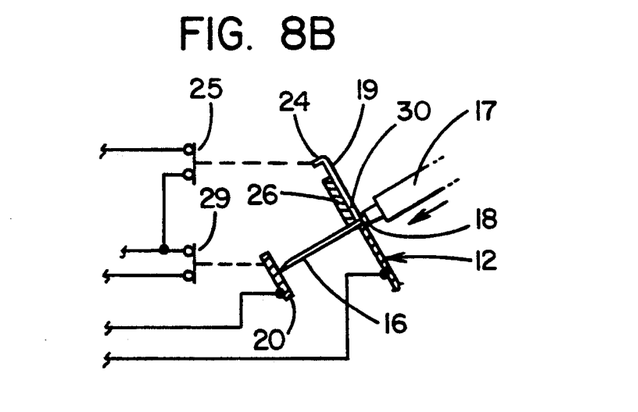

FIGS. 8A and 8B demonstrate the electrical circuitry involved in the within apparatus. FIG. 8A indicates the electrical configuration prior to the insertion of a needle into grommet 15. It can be seen from FIG. 8 that insertion and actuation of actuator switch 25 activates current flow as between the first electrical contact 13 and second electrical contact 34. Due to the conductive nature of the first conductive plate 12 and second conductive plate 20, an electrical gradient is created there between through metallic needle shaft 16. Additionally, movement of second conductive plate 20 actuates second actuator switch 29. This, in turn, permits electrical current to flow to light 14, exhaust motor 35 and fan time delay 36. Exhaust fan 31 starts immediately but is delayed in its termination due to the aforesaid fan time delay 36.

OPERATION

The apparatus, once plugged into a standard receptacle or some other suitable means, is continuously ready for operation. An individual inserts needle shaft 16 into grommet 15 until needle hub 18 presses against first conductive plate 12 thereby forcing first conductive plate 12 to be flexed inwardly. Inwardly curving leading edge 24 actuates actuator switch 25 which allows current to flow as between the first electrical contact 13 and second electrical contact 34. Current flows through the aforesaid contacts and, therefore, the first conductive plate 12 and second conductive plate 20. Needle shaft 16 in essences closes the circuit and thereupon needle shaft 16 is immediately incinerated. Literally, the time necessary to accomplish complete and absolute incineration is measured in virtual milliseconds.

In addition to the foregoing, as needle shaft 16 is first inserted into the housing it engages second conductive plate 20 and pushes it inwardly. Second actuator switch 29 is closed and light 14 is energized. This then demonstrates that the unit is operational and ready to accomplish the afore described incineration process. Additionally, closure of the circuit from second actuator switch 29 energizes exhaust motor 35 and fan time delay 36. Exhaust fan 31 starts immediately and, due to fan time delay 36, continues to run for approximately ten to twenty seconds after needle incineration and deactivation of the second actuator switch 29 through return of second conductive plate 20 to its first position. Also, return of second conductive plate 20 to its first position turns off light 14 and the machine is, once again, ready for another needle to be inserted for incineration.

The byproducts of needle disintegration fall harmlessly into bottom 5 of housing 1 for subsequent disposal as ordinary trash due to its innocuous and harmless character.

What is claimed is:

1. An apparatus for disintegrating syringe needles as a means of needle disposal, comprising:
   A) a housing containing a grommet defined opening therein capable of receiving used syringe needles;
   B) a flexible first conducive plate substantially "V" shaped as defined by a pair of leg portions so as to accept a vast majority of all diameters and sizes of syringe needles and mounted within said housing and so disposed as to contact the needle immediately upon insertion of the needle into said housing;
   C) a second conductive plate mounted within said housing in a spring biased first position immediately adjacent and substantially parallel to said first conductive plate slidably movable within said housing on a plurality of escort rods so as to remain substantially parallel to the first conductive plate through its movement to a second position so as to accommodate variously sized needle shaft lengths;
   D) a first electrical contact engaged upon the first conductive plate;
   E) a second electrical contact engaged upon the second conductive plate;
   F) connection of a power source to the first and second electrical contacts, and;
   G) a normally open actuator switch arranged so as to be activated by pressure from said first conductive plate flexing inwardly upon the entire needle shaft being inserted into said housing and the needle hub thereof in contract with the first conductive plate, thereby providing electrical flow as between the first and second electrical contacts of sufficient character to incinerate the entire needle shaft.

2. The syringe needle disintegrating device of claim 1 wherein one of the leg portions of the first conductive plate contains an inwardly curving leading edge which extends beyond the plane of said first conductive plate and is in proximity to said actuator switch so as to activate same as the first conductive plate flexes inwardly as a result of pressure from a syringe needle hub.

3. The syringe needle disintegrating device of claim 1 further comprising a second actuator switch mounted within said housing and disposed so as to be open when the second conductive plate is in its first position and closed as the second conductive plate moves to its second position thereby creating an electric circuit and energizing a light or other sound emitting device so as to indicate device operation.

4. The syringe needle disintegrating device of claim 3 wherein said second actuator switch also energizes an exhaust motor and fan and, simultaneously, fan time delay means enables exhaust motor and fan to continue to run after return of the second conductive plate to its first position and terminates electric current so as to remove any gases or toxins from within the housing.

5. The syringe needle disintegrating device of claim 1 further comprising an exhaust motor and fan in an end of the housing, said exhaust fan discharging air through a filter encased in a filter housing thereby trapping or alleviating the passage of airborne pathogens or other unwanted material out of the housing.

6. The syringe needle disintegrating device of claim 1 further comprising a flash back inhibitor attached by screw and insulator means and arranged spatially between said first and second conductive plates so as to be compressed by the inward flexing of the first conductive plate thereby coming into contact with a needle shaft and directing the needle shaft downward to maintain strict contact with the first conductive plate for enhanced electrical current flow through said needle shaft.

7. The syringe needle disintegrating device of claim 6 wherein said flash back inhibitor is spatially arranged so as to eliminate flashback or needle particulates from being propelled back through the grommet.

8. The syringe needle disintegrating device of claim 1 wherein said second conductive plate is mounted on an escort block and further adapted to escort rods for movement within said housing to a second position substantially parallel to the first conductive plate a distance of sufficient length to accomplish incineration of any needle shaft length.

9. A method of disintegrating the entire needle shaft of a syringe needle comprising the steps of:
   A) inserting a needle shaft through a needle receiving means with grommet guide means, said needle shaft coming into contact with both a first conductive plate and then, immediately thereafter, a second conductive plate slidably movable within said housing substantially parallel to the first conductive plate;
   B) flexing of the first conducive plate as it comes in integral contact with a needle hub of a syringe needle thereby pressure activating an actuating switch and enabling current to flow as between first and second electrical contacts mounted on the first and second conductive plates, said needle shaft thereby closing the circuit between the contacts and incinerating the needle shaft completely and leaving only a needle remnant formed in a fused caplike configuration.

10. The method of claim 9 wherein smoke or other remnants of incineration are removed from within the apparatus housing by means of an exhaust fan and motor.

* * * * *